(12) United States Patent
Sampalis

(10) Patent No.: US 8,057,825 B2
(45) Date of Patent: Nov. 15, 2011

(54) KRILL EXTRACTS FOR TREATMENT OF CARDIOVASCULAR DISEASES

(75) Inventor: Tina Sampalis, Laval (CA)

(73) Assignee: Neptune Technologies & Bioressources Inc., Laval (CA)

( * ) Notice: Subject to any disclaimer, the term of this patent is extended or adjusted under 35 U.S.C. 154(b) by 1180 days.

(21) Appl. No.: 11/640,235

(22) Filed: Dec. 18, 2006

(65) Prior Publication Data

US 2007/0098808 A1     May 3, 2007

Related U.S. Application Data

(62) Division of application No. 10/481,040, filed as application No. PCT/CA02/00843 on Jun. 7, 2002, now abandoned.

(60) Provisional application No. 60/298,383, filed on Jun. 18, 2001.

(51) Int. Cl.
*A61K 35/36*     (2006.01)

(52) U.S. Cl. .......................... 424/522; 424/520

(58) Field of Classification Search .................. None
See application file for complete search history.

(56) References Cited

U.S. PATENT DOCUMENTS 6,265,450 B1     7/2001     Asami et al.

FOREIGN PATENT DOCUMENTS

JP     60-153779     8/1985
WO     WO 00/23546 A1     4/2000

OTHER PUBLICATIONS

"Marine." Merriam-Webster Online Dictionary. 2010. Merriam-Webster Online. Retrieved Jun. 11, 2010 from URL: <http://www.merriam-webster.com/dictionary/marine>.*
Saynor et al, Lipids, 1992, vol. 27, No. 7, pp. 533-538.*
The Merck Manual, Berkow (ed.), 1992, Merck Research Laboratories, 16$^{th}$ Edition, pp. 409-429.*
Mori et al. American Journal of Clinical Nutrition, 2000, vol. 71, pp. 1085-1094.*
Co-pending U.S. Appl. No. 10/435,094; Inventor: Sampalis, Fontini; filed Jul. 13, 2004.*
Robert Berkow, et al., "Generalized Cardiovascular Disorders", The Merck Manual of Diagnosis and Therapy, 1992, pp. 409-431, Chapter 24, Merck Research Laboratories, Rahway, NJ, USA.
Tova Navarra et al., Encyclopedia of Vitamins, Minerals and Supplements, 1996, pp. 134, 141-142, Facts on File, Inc., USA.

* cited by examiner

*Primary Examiner* — Allison Ford
(74) *Attorney, Agent, or Firm* — Crowell & Moring LLP

(57) ABSTRACT

The present invention relates to a method of treatment and/or prevention of cardiovascular disease, rheumatoid arthritis, skin cancer, premenstrual syndrome, diabetes and transdermal transport enhancement. The method comprises the administration of a therapeutically effective amount of krill and/or marine oil to a patient. The present invention also relates to a composition for the treatment and/or prevention of these diseases.

12 Claims, No Drawings

KRILL EXTRACTS FOR TREATMENT OF CARDIOVASCULAR DISEASES

BACKGROUND OF THE INVENTION

1. Field of the Invention

This invention relates to multi-therapeutic extracts derived from krill and/or marine, which can prevent and/or treat several diseases.

2. Description of Prior Art

Krill is the common name for small, shrimp-like crustaceans, however not shrimp, that swarm in dense shoals, especially in Antarctic waters. It is one of the most important food source for fish, some kind of birds and especially for baleen whales as being an important source of protein. Krill is also a good source of omega-3 fatty acid, which are well known for their health benefits.

It is known in the art to use krill and/or marine enzymes for the treatment of a great variety of diseases in human and animals such as infections, inflammations, cancers, HIV/AIDS, pain, polyps, warts, hemorrhoids, plaque, wrinkles, thin hairs, allergic itch, anti-adhesion, eye disease, acne, cystic fibrosis and immune disorders including autoimmune disease and cancer.

It is also known in the art that krill and/or marine oil may be used for the treatment of autoimmune murine lupus and other autoimmune diseases and can also be used for treating cardiovascular diseases.

However, the krill and/or marine oil used for these treatments has only conserved its omega-3 fatty acids as active ingredients, which is a very small part of all the active ingredients of the krill and/or marine itself. This fact reduces the potential of the krill and/or marine oil as a treatment for these diseases.

There is an increasing demand for treatments using products derived from a natural source, therefore, it would be highly desirable to be provided with a krill and/or marine extract having an enhanced potential for prevention and/or treatment and/or management of disease.

SUMMARY OF THE INVENTION

In accordance with the present invention there is provided a method of prevention, therapy and/or treatment of several disease, the method comprising the administration of a therapeutically effective amount of krill and/or marine oil to a patient.

In a preferred embodiment of the present invention the krill and/or marine oil is obtained from a process comprising the steps of:

(a) placing krill and/or marine material in a ketone solvent, preferably acetone to achieve extraction of the soluble lipid fraction from the marine and/or aquatic animal material;

(b) separating the liquid and solid contents;

(c) recovering a first lipid rich fraction from the liquid contents by evaporation of the solvent present in the liquid contents;

(d) placing the solid contents in an organic solvent selected from the group of solvents consisting of alcohol, preferably ethanol, isopropanol or t-butanol and esters of acetic acid, preferably ethyl acetate to achieve extraction of the remaining soluble lipid fraction from the marine and/or aquatic material;

(e) separating the liquid and solid contents;

(f) recovering a second lipid rich fraction by evaporation of the solvent from the liquid contents; and (g) recovering the solid contents.

In a preferred embodiment of the present invention, the krill and/or marine oil comprises Eicosapentanoic acid, Docosahexanoic acid, Phosphatidylcholine, Phosphatidylinositol, Phosphatidylserine, Phosphatidylethanolamine, Sphingomyelin, a-tocopherol, all-trans retinol, Astaxanthin and flavonoid.

In another embodiment of the present invention, the krill and/or marine oil comprises Eicosapentanoic acid, Docosahexanoic acid, Linolenic acid, Alpha-linolenic acid, Linoleic acid, Arachidonic acid, Oleic acid, palmitic acid, palmitoleic acid, stearic acid, nervonic acid, Phosphatidylcholine, Phosphatidylinositol, Phosphatidylserine, Phosphatidylethanolamine, Sphingomyelin, Cholesterol, Triglycerides, Monoglycerides, a-tocopherol, all-trans retinol, Astaxanthin, Canthaxanthin, β-carotene, flavonoid, Zinc, Selenium, sodium, potassium and calcium.

In another embodiment of the present invention, the krill and/or marine oil comprises Eicosapentanoic acid, Docosahexanoic acid, Linolenic acid, Alpha-linolenic acid, Linoleic acid, Arachidonic acid, Oleic acid, palmitic acid, palmitoleic acid, stearic acid, Phosphatidylcholine, Phosphatidylinositol, Phosphatidylserine, Phosphatidylethanolamine, Sphingomyelin, Cholesterol, Triglycerides, Monoglycerides, a-tocopherol, all-trans retinol, Astaxanthin, Canthaxanthin, β-carotene, Zinc and Selenium.

The diseases that can be treated and/or prevented by the method of the present invention are cardiovascular diseases, arthritis, skin cancer, diabetes, premenstrual syndrome and transdermal transport enhancement.

In accordance with the present invention there is also provided a composition for the treatment and/or prevention and/or therapy of the previously mentioned diseases, the composition comprising a therapeutically effective amount of krill and/or marine oil in association with a pharmaceutically acceptable carrier.

In accordance with the present invention, it is further provided the use of krill and/or marine oil for the treatment and/or prevention and/or therapy of the previously mentioned diseases.

In accordance with the present invention, it is also provided the use of krill and/or marine oil for the manufacture of a medicament for the treatment and/or prevention and/or therapy of the previously mentioned diseases.

DETAILED DESCRIPTION OF THE INVENTION

In accordance with the present invention, there is provided krill and/or marine extract for prevention and/or treatment and/or therapy of several diseases.

A multi-therapeutic oil extract free of enzyme is derived from krill and/or marine, found in any marine environment around the world, for example, the Antarctic ocean (euphasia superba), the Pacific ocean (euphasia pacifica), the Atlantic ocean, the Indian ocean, in particular coastal regions of Mauritius Island and/or Reunion Island of Madagascar, Canadian West Coast, Japanese Coast, St-Lawrence Gulf and Fundy Bay, and this oil extract is a free fatty acid lipid fraction.

The extraction process can be described as the following:

(a) Placing marine and/or aquatic krill and/or marine in a ketone solvent, preferably acetone, to achieve the extraction of grease from the krill and/or marine;

(b) Separating the liquid and the solid phases;

(c) Recovering a lipid rich fraction from the liquid phase obtained at step (b) by evaporation of the solvent present in the liquid phase;

(d) Placing the solid phase in an organic solvent, which can be alcohol, preferably ethanol, isopropanol or t-butanol, or esters of acetic acid, preferably ethyl acetate. This in order to extract the remaining soluble lipid fraction from the solid phase;

(e) Separating the liquid and the solid phases; and (f) Recovering a lipid rich fraction from the liquid phase obtained at step (e) by evaporation of the solvent present in the liquid phase.

The active components of the enzyme-free krill and/or marine oil extract are:

Lipids
i) Omega-3:
i. Eicosapentanoic acid: >8 g/100 g
ii. Docosahexanoic acid: >2 g/100 g
iii. Linolenic acid: >0.10 g/100 g
iv. Alpha-linolenic acid: >0.3 g/100 g
In the preferred embodiment of the present invention, the Omega-3 are found in more than 30 g/100 g.
ii) Omega-6: i. Linoleic acid: >0.9 g/100 g
ii. Arachidonic acid: <0.45 g/100 g, preferably <0.6 g/100 g
iii) Omega-9: i. Oleic acid: >5 g/100 g
iv) palmitic acid: >10 g/100 g
v) palmitoleic acid: 0.08 g/100 g
vi) stearic acid: >0.5 g/100 g
Phospholipids
Phosphatidylcholine: >4.5 g/100 g
Phosphatidylinositol: >107 mg/100 g
Phosphatidylserine: >75 mg/100 g
Phosphatidylethanolamine: >0.5 g/100 g
Sphingomyelin: >107 mg/100 g
Neutral Lipids
Cholesterol: <3 g/100 g
Triglycerides: <55 g/100 g
Monoglycerides: >0.5 g/100 g
In another embodiment of the present invention, the neutral lipids of the krill and/or marine extract also comprises:
Diglycerides: >0.5 g/100 g
Antioxydants
α-tocopherol (vitamin E): >1.0 IU/100 g
all-trans retinol (vitamin A): >1500 IU/100 g
β-carotene: >3000 μg/100 ml
Pigments
Astaxanthin: >20 mg/100 g
Canthaxanthin: >2 mg/100 g
Metals
Zinc: >0.1 mg/100 g
Selenium: >0.1 mg/100 g
In another embodiment of the present invention, the krill and/or marine extract also comprises:
Flavonoids: >0.5 mg/100 g
Sodium: <500 mg/100 g
Calcium: >0.1 mg/100 g
Potassium: >50 mg/100 g
Aluminum: <8.5 mg/100 g
Protein: >4 g/100 g
Moisture and volatile matter: <0.8%

After characterization of the krill and/or marine oil extract, it was determined that the extract contains less than 25 ppm of solvent residue from the extraction process.

The oil has the following stability indexes:
Peroxide value: <0.1 (mEq/kg)
Oil Stability index: <0.1 after 50 hours at 97.8° C.
Saponification index: 70-180
Iodine value: 60-130%

The present invention will be more readily understood by referring to the following examples which are given to illustrate the invention rather than to limit its scope.

EXAMPLE 1

Cardiovascular Disease Prevention and/or Treatment

Krill and/or marine oil has been shown to decrease cholesterol in vivo. It also inhibits platelet adhesion and plaque formation and reduces vascular endothelial inflammation in a patient. It can offer hypertension prophylaxis. It prevents oxidation of low-density lipoprotein. It may have an inhibitory effect on the secretion of VLDL due to increased intracellular degradation of apo B-100. It also offers a post-myocardial infarction prophylaxis because of its ability to decrease CIII apolipoprotein B, to decrease CIII non-apolipoprotein B lipoproteins and to increase antithrombin III levels. Krill and/or marine oil is suitable for prophylactic usage against cardiovascular disease in human where cardiovascular disease relates to coronary artery disease, hyperlipidemia, hypertension, ischemic disease (relating to angina, myocardial infarction, cerebral ischemia, shock without clinical or laboratory evidence of ischemia, arrhythmia)

To evaluate the effects of krill and/or marine oil on the course of arteriosclerotic coronary artery disease and hyperlipidemia, a study was performed (prospective clinical trial, statistical significance $p<0.05$) with patients with known hyperlipidemia.

A group of 13 patients took krill and/or marine oil concentrate gelules. Both fish oil and krill and/or marine oil contained equal amounts of omega-3 fatty acids. Recommended dosage is of 1 to 6 capsules per day, each capsule containing 800 mg of oil. In this study, each patient took 6 capsules per day.

The patients were tested for LDL, HDL, Triglycerides, vital signs, CBC, SGOT/SGPT, γ-GT, ALP, Urea, Creatine, Glucose, $K^+$, $Na^+$, $Ca^{2+}$ and total indirect bilirubin cholesterol before treatment and also at 2 months.

Table 1 is showing the results obtained from the previously described tests:

TABLE 1

| | Paired Samples Test Paired Differences | | | | | | | |
|---|---|---|---|---|---|---|---|---|
| Parameter | | | Std. Error | 95% Confidence Interval of the Difference | | | | Sig. |
| tested | Mean | SD. | Mean | Lower | Upper | t-value | df | (2-tailed) |
| Cholesterol | .4954 | .55800 | .15476 | .1582 | .8326 | 3.201 | 12 | .008 |
| Triglycerides | .3538 | .54543 | .15127 | .0242 | .6834 | 2.339 | 12 | .037 |
| HDL | −.2108 | .29859 | .08281 | −.3912 | −.0303 | −2.545 | 12 | .026 |

TABLE 1-continued

Paired Samples Test
Paired Differences

| Parameter tested | Mean | SD. | Std. Error Mean | 95% Confidence Interval of the Difference Lower | Upper | t-value | df | Sig. (2-tailed) |
|---|---|---|---|---|---|---|---|---|
| LDL | .2846 | .47333 | .13128 | −.0014 | .5706 | 2.168 | 12 | .051 |
| Chol/HDL | .3600 | .53446 | .14823 | .0370 | .6830 | 2.429 | 12 | .032 |

From the above, it was shown that a daily uptake of 1 to 4.8 g of krill extract was providing to the patients a cholesterol decrease in the range of 15%, a triglycerides decrease in the range of 15%, a HDL increase in the range of 8%, a LDL decrease in the range of 13% and a Cholesterol/HDL ratio decrease of 14%.

This shows that an uptake of krill extract has a beneficial effect on patient suffering from hyperlipidemia, which is known to be the primary causative factor of atherosclerosis.

EXAMPLE 2

Arthritis Treatment

Krill and/or marine oil offers symptomatic relief for Arthritis where arthritis relates to adult arthritis, Still's disease, polyarticular or pauciarticular juvenile rheumatoid arthritis, rheumatoid arthritis, osteoarthritis because it has been shown that it provides a clinical improvement in decreasing the number of tender joints and of analgesics consumed daily by decreasing the production of Interleukin-8 and Interleukin-1 in human patients. Patients with a bleeding tendency or severe psychiatric disease were excluded from the study.

To evaluate the effects of krill and/or marine oil supplementation on the clinical course of osteoarthritis, a study was performed (prospective clinical trial, statistical significance $p<0.05$) with patients diagnosed with and treated for osteoarthritis which is Active class I, II or III and having treatment with NSAIDs and/or analgesics for at least 3 months before enrollment.

A group of 13 patients took krill and/or marine oil concentrate capsules at a daily rate of 6 capsules of 800 mg krill oil per capsule. The recommended dosage varies between 1 and 4.8 grams of pure krill extract per day. Patients were asked to follow a normal healthy diet consisting of 20% fat (less than 10% animal fat), 40% protein and 40% carbohydrates.

The inclusion criteria for the study are being aged between 50 and 65 years, both genders being admissible, having a clinical diagnosis of primary osteoarthritis (mild to moderate) 6 to 12 months prior to study enrollment including pain and stiffness, radiographic confirmation of illness prior to enrollment. It also include evidence of measurable symptoms of OA for at least 3 months prior to study enrollment requiring the use of acetaminophen, anti-inflammatory agents or opioid analgesics. Patients were asked to stop the use of all "painkillers" the week prior to initiation of the trial for wash-out purposes.

The Exclusion criteria were a severe osteoarthritis, unavoidable sustained use of NSAID's, aspirin or other medicines for anti-inflammatory use, use of topical analgesics within 4 weeks of randomization visit, steroid injection into either knee within past 3 months, initiation of physical therapy or muscle conditioning within 3 months, seafood allergies, use of anticoagulants or salicylates, alcohol consumption exceeding 3 mixed drinks per day, concurrent medical/arthritic disease that could confound or interfere with the evaluation of pain, prior surgery (including arthroscopy) of either knee, a known "secondary" cause of osteoarthritis.

Evaluation was based on daily dose of NSAIDs and/or analgesics and/or SAARDs, number of painful joints, number or swollen joints, duration of morning stiffness, visual analog scale (0-100) WOMAC scale and SF36. Preliminary results have been obtained after 2 months. The number of NSAIDs and/or analgesics and/or SAARDs required for daily functioning has been recorded at initiation and at 2 months after initiation.

Results shown at Table 2 demonstrate the effect of an uptake of krill extract on the relief of arthritis.

TABLE 2

| | Frequency | % | Valid % | Cumulative % |
|---|---|---|---|---|
| No change | 3 | 23.1 | 23.1 | 23.1 |
| Pain relief | 10 | 76.9 | 76.9 | 100.0 |
| Total | 13 | 100.0 | 100.0 | |

This shows that ten out of 13 (76.9%) people reported a significant pain relief and improvement of flexibility of large joints (lower back, knees, shoulders)

EXAMPLE 3

Skin Cancer Prophylaxis

Krill and/or marine oil has been shown to be a skin cancer prophylactic because of its retinol anti-carcinogenic effect, Astaxanthin anti-carcinogenic effect and its phopholipid anti-carcinogenic effect.

To evaluate the photoprotective potential of krill and/or marine oil against UVB-induced skin cancer, a study was performed on nude mice, preferably on C57BL6 Nude Congenic Mice-B6NU-T (heterozygotes) because of their proven susceptibility to skin cancer.

Groups were formed as follows: 48 fish oil: 16 with oral supplementation (po) 16 with local application, 16 with po and local application; 48 krill and/or marine oil: 16 with po, 16 with local application, 16 with po and local application. In order to establish efficacy of krill and/or marine oil for the prevention of skin cancer, the test was conducted as a randomized blind controlled trial (statistical significance $p<0.05$). Half of the mice have been treated orally or topically or both with oil containing 100% by weight krill and/or marine oil and the other half have been treated the same way with fish oil.

Nutrition was fat-free chow for the first week and was modified accordingly with the assigned group as described below for the following 2-20 weeks in the quantity of 1 ml of oil per day.

The mice were divided in six groups as follows:
Group A: fat-free chow with supplementation of fish oil (20% of total calories)
Group B: fat-free chow (100% of calories)+local application of fish oil 2 times per day
Group C: fat free chow with supplementation of fish oil (20% of total calories)+local application of soy oil 2 times per day
Group D: fat-free chow with supplementation of krill and/or marine oil (20% of total calories)
Group E: fat free chow (100% of calories)+local application of krill and/or marine oil 2 times per day
Group F: fat-free chow with supplementation or krill and/or marine oil (20% of total calories)+local application of krill and/or marine oil 2 times per day The mice had been submitted to UVB radiation using a fluorescent test lamp, emission spectrum 270-400 nm during weeks 2-20. The essay were performed during 30 minutes of UVB exposure per day and the test lamp was at a distance of 30 cm from the mice. At the end of the 20 weeks, or when malignant tumors had formed, mice were anesthetized with ether and sacrificed. Skin was examined blind by pathologists for signs of carcinogenesis.

The following tables (Tables 3-8) are showing the results obtained about the incidence of cancer when ultra-violet radiations are administered to mice's skin during 5 weeks.

TABLE 3

Krill extract Oral uptake

| | | Frequency | Percent | Valid Percent | Cumulative Percent |
|---|---|---|---|---|---|
| Valid | Benign | 14 | 87.5 | 87.5 | 87.5 |
| | Cancer | 2 | 12.5 | 12.5 | 100.0 |
| | Total | 16 | 100.0 | 100.0 | |

TABLE 4

Control Oral uptake

| | | Frequency | Percent | Valid Percent | Cumulative Percent |
|---|---|---|---|---|---|
| Valid | Benign | 14 | 87.5 | 87.5 | 87.5 |
| | Cancer | 2 | 12.5 | 12.5 | 100.0 |
| | Total | 16 | 100.0 | 100.0 | |

TABLE 5

Krill extract topical uptake

| | | Frequency | Percent | Valid Percent | Cumulative Percent |
|---|---|---|---|---|---|
| Valid | BENIGN | 16 | 100.0 | 100.0 | 100.0 |

TABLE 6

Control topical uptake

| | | Frequency | Percent | Valid Percent | Cumulative Percent |
|---|---|---|---|---|---|
| Valid | BENIGN | 5 | 31.3 | 31.3 | 31.3 |
| | Cancer | 11 | 68.8 | 68.8 | 100.0 |
| | Total | 16 | 100.0 | 100.0 | |

TABLE 7

Krill extract topical and oral uptake

| | | Frequency | Percent | Valid Percent | Cumulative Percent |
|---|---|---|---|---|---|
| Valid | BENIGN | 16 | 100.0 | 100.0 | 100.0 |

TABLE 8

Control topical and oral uptake

| | | Frequency | Percent | Valid Percent | Cumulative Percent |
|---|---|---|---|---|---|
| Valid | BENIGN | 10 | 62.5 | 62.5 | 62.5 |
| | Cancer | 6 | 37.5 | 37.5 | 100.0 |
| | Total | 16 | 100.0 | 100.0 | |

The results obtained shows that both oral and topical use of krill oil is effective for the protection of the skin against the harmful effects fo UVB radiation induced skin cancer.

EXAMPLE 4

Transdermal Transport in Therapeutic Applications

Krill and/or marine oil enhances transdermal transportation as a substrate for dermatological topical therapeutic applications. It may be used in dermatological treatments via creams, ointments, gels, lotions and oils. It may also be used in various therapeutic applications such as relating to anesthesic, corticosteroids, anti-inflammatory, antibiotic and ketolytic functions.

To evaluate the efficacy of krill and/or marine oil as a substrate for topical treatments and the speed of transdermal absorption of krill and/or marine alone or as a substrate, a study was performed as a randomized blind controlled trial on C57BL6 nude Congenic Mice-B6NU-T (heterozygotes).

The results appearing in tables 5 and 6 are showing that topical treatment with krill oil faciliate the absorption of retinol and other antioxydants through the dermis which in turn result in significant photoprotective potential which in turn results in 100% protection from UVB induced skin cancer. In contrast, fish oil application with all-trans retinol resulted in 68.8% incidence of cancer.

EXAMPLE 5

Transdermal Transport for Dermatological Topical Cosmetic Applications

Krill and/or marine oil can be used to enhance transdermal transportation as a substrate for dermatological topical cosmetic applications where cosmetic applications relate to skin hydration, anti-wrinkle, keratolytics, peeling and mask via creams, ointments, gels, lotions or oils.

To evaluate the effects of Krill and/or marine oil in aging and facial wrinkles, a study was conducted as a prospective clinical trial on patients concerned about facial dryness and wrinkles. Those patients had no prognosis severely limited by other dermatological or non-dermatological condition, bleeding tendency or severe psychiatric disease.

13 Healthy Caucasian women with facial dryness or wrinkles have been included in this study. Women have been asked to take 6 capsules a day, each capsule containing 800 mg of krill extract. The recommended daily dosage is of about 1 to 4.8 g of krill extract.

Table 9 shows results obtained on skin hydration following the method previously described.

TABLE 9

Changes in skin hydration

|  | Frequency | % | Valid % | Cumulative % |
|---|---|---|---|---|
| No change | 4 | 30.8 | 30.8 | 30.8 |
| Hydration | 9 | 69.2 | 69.2 | 100.0 |
| Total | 13 | 100.0 | 100.0 |  |

The results of the pilot study after 2 months indicate that nine out of 13 (69.2%) people reported a significant improvement of the hydration, texture and elasticity of the skin (face, hands and arms) in human patients.

Moreover, these results are also indicative that krill extract is useful for anti-wrinkle treatment. The mechanism of all-trans retinol, which is included in the krill oil, as an anti-wrinkle works as follows:
 Regeneration and distinctive anti-inflammatory effects
 Improve blood irrigation
 Increases the epidermis regeneration by increasing the rate of cell division and turnover
 Accelerates the differentiation of keratin
 Regenerates the collagen
 Allows cells in the top layer of the skin, which are always being replaces, to mature more normally than untreated sun-damaged cells
 Reduces the activation of enzymes that break down the proteins collagen and elastin that provide structural support for the skin.

The results obtained with krill extract administered on a patent's skin show that the krill extract is having an anti-wrinkle effect by increasing the hydration and the mechanism above described.

EXAMPLE 6

Premenstrual Syndrome

Table 10 shows results obtained from the use of krill oil to reduce the pain and mood changes associated with premenstrual syndrome in women. Krill oil extract was administered to 7 women during 2 months. The women were taking 6 capsules of krill extract per day, each capsule containing 800 mg of krill oil. A recommended daily intake of krill oil is of about 1 to 4.8 grams. All participants were advised to continue with their usual nutrition habits and to refrain from initiating any restrictions in their diet. No serious side effects were reported.

All women enrolled reported noticeable emotional and/or physical discomfort 7 to 10 days prior to menstruation. A self-assessment visual analogue scale validated for the assessment of the premenstrual syndrome, ranging from 0 (no symptoms) to 10 (unbearable) was used as a primary outcome in order to evaluate the effect of krill extract on premenstrual discomfort.

Data analysis has been reported on 60% of the women participating in the study who have completed a two months regimen. The majority of the women (73.3%) showed a clinically significant reduction in both emotional and physical distress prior to menstruation (see Table 10).

TABLE 10

Frequency distribution of the effect of krill extract on premenstrual syndrome symptomatology

| PMS symptoms | Frequency % | Valid % | Cumulative % |
|---|---|---|---|
| No change | 26.7 | 26.7 | 26.7 |
| Positive | 73.3 | 73.3 | 100.0 |
| Total | 100.0 | 100.0 |  |

EXAMPLE 7

Diabetes 8 human patients were taking krill extract at the dosage of 6 capsules a day, each capsule containing 800 mg of krill extract, during 2 months. A recommended daily intake of krill oil is of about 1 to 4.8 grams. The Table 11 is showing the variation in the glucose tested for the patients after 2 months.

TABLE 11

Variation in glucose in patients
Paired Differences

| Parameter tested | Mean | SD. | Std. Error Mean | 95% Confidence Interval of the Difference | t-value | df | Sig. (2-tailed) |
|---|---|---|---|---|---|---|---|
| Glucose | .5778 | .60369 | .20123 | .1137-1.0418 | 2.871 | 8 | .021 |

A blood glucose decrease of 20% was obtained for the patients taking krill extract, which shows that an uptake of krill extract is controlling blood glucose content and therefore controlling diabetes in human patients.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of reducing cholesterol in a human, said method comprising administering to a human in need thereof an amount of krill extract effective to reduce cholesterol in said human, wherein said krill extract comprises eicosapentanoic acid and docosahexanoic acid.

2. The method of claim 1, wherein said krill extract comprises Eicosapentanoic acid, Docosahexanoic acid, phospholipids and an antioxidant.

3. The method of claim 2, wherein said phospholipids are at least one selected from the group consisting of Phosphatidylcholine, Phosphatidylinositol, Phosphatidylserine, Phosphatidylethanolamine and Sphingomyelin.

4. The method of claim 2, wherein said antioxidant is at least one selected from the group consisting of α-tocopherol, astaxanthin and flavonoid.

5. The method of claim 2, wherein said krill extract further comprises at least one compound selected from the group consisting of Linoleic acid, Alpha-linoleic acid, arachidonic acid, oleic acid, palmitic acid, palmitoleic acid, stearic acid, cholesterol, triglycerides, monoglycerides, all-trans retinol, canthaxanthin, β-carotene, zinc, selenium, nervonic acid, sodium, potassium and calcium.

6. The method of claim 1, wherein said administering is effected orally.

7. A method for reducing platelet adhesion and plaque formation in a human comprising administering to a human in need thereof an amount of krill extract effective to reduce platelet adhesion and/or plaque formation in said human, and wherein said krill extract comprises eicosapentanoic acid and docosahexanoic acid.

8. The method of claim 7, wherein said krill extract comprises Eicosapentanoic acid, Docosahexanoic acid, phospholipids and an antioxidant.

9. The method of claim 8, wherein said phospholipids are at least one selected from the group consisting of Phosphatidylcholine, Phosphatidylinositol, Phosphatidylserine, Phosphatidylethanolamine and Sphingomyelin.

10. The method of claim 8, wherein said antioxidant is at least one selected from the group consisting of α-tocopherol, astaxanthin and flavonoids.

11. The method of claim 8, wherein said krill extract further comprises at least one compound selected from the group consisting of Linoleic acid, Alpha-linoleic acid, arachidonic acid, oleic acid, palmitic acid, palmitoleic acid, stearic acid, cholesterol, triglycerides, monoglycerides, all-trans retinol, canthaxanthin, β-carotene, zinc, selenium, nervonic acid, sodium, potassium and calcium.

12. The method of claim 7, wherein said administering is effected orally.

\* \* \* \* \*